United States Patent [19]

King

[11] Patent Number: 5,498,528
[45] Date of Patent: Mar. 12, 1996

[54] DETECTION OF HELICOBACTER PYLORI

[76] Inventor: Wing King, 641 48th Ave., San Francisco, Calif. 94121

[21] Appl. No.: 257,862

[22] Filed: Jun. 10, 1994

[51] Int. Cl.$^6$ .............................. C12Q 1/04; C12Q 1/02; G01N 33/48; G01N 33/20
[52] U.S. Cl. .................... 435/34; 435/29; 435/4; 435/810; 436/63; 436/74
[58] Field of Search ....................... 435/34, 29, 4, 435/7.32, 7.92, 7.93, 7.94, 810; 436/513, 501, 63, 74

[56] References Cited

U.S. PATENT DOCUMENTS

| | | | |
|---|---|---|---|
| 4,101,382 | 7/1978 | Chang | 195/103.5 |
| 4,282,316 | 8/1981 | Modrovich | 435/12 |
| 4,748,113 | 5/1988 | Marshall | 435/12 |
| 4,923,801 | 5/1990 | Marshall et al. | 435/34 |
| 4,947,861 | 8/1990 | Hamilton | 128/719 |
| 5,200,344 | 4/1993 | Blaser et al. | 435/7.92 |
| 5,262,156 | 11/1993 | Alemohammad | 435/7.92 |
| 5,286,492 | 2/1994 | Dettmar et al. | 435/34 |

FOREIGN PATENT DOCUMENTS

| | | |
|---|---|---|
| 1650701 | 5/1991 | U.S.S.R. |
| WO226282 | 11/1993 | WIPO |
| WO93/22682 | 11/1993 | WIPO |

OTHER PUBLICATIONS

Cellini et al, J. Clin Micro., vol. 30, pp. 1351–1353, May 1992.
Tee et al, J. Clin Micro., vol. 29, No. 11, pp. 2587–2589, (1991).
Cellini et al., "New Plate Medium for Growth and Detection of Urease Activity of *Helicobacter pylori,*" *J. Clin. Microbiol.* (1992) 30:1351–1353.
Endtz et al., "Comparison of Six Media, Including a Semisolid Agar, for the Isolation of Various *Campylobacter* Species from Stool Specimens," *J. Clin. Microbiol.* (1991) 29:1007–1010.
Ferguson et al., "Isolation of *Helicobacter pylori* from Saliva," *J. Clin. Microbiol.* (1993) 31:2802–2804.
McNulty and Wise, letter, "Rapid Diagnosis of Campylobacter–Associated Gastritis," *Lancet* (1985) pp. 1443–1444.
Schrader et al., "A Role for Culture in Diagnosis of *Helicobacter pylori*–Related Gastric Disease," *Am. J. Gastroenterology* (1993) 88:1729–1733.
Secker et al., "Gas–Permeable Lifecell Tissue Culture Flasks Give Improved Growth of *Helicobacter pylori* in a Liquid Medium," *J. Clin. Microbiol.* (1991) 29:1060–1061.
Shahamat et al., "Evaluation of Liquid Media for Growth of *Helicobacter pylori,*" *J. Clin. Microbiol.* (1991) 29:2835–2837.
Tee et al., "Comparative Evaluation of Three Selective Media and a Nonselective Medium for the Culture of *Helicobacter pylori* from Gastric Biopsies," *J. Clin. Microbiol.* (1991) 29:2587–2589.
Xia et al., "Enhanced Cultivation of *Helicobacter pylori* in Liquid Media," *J. Clin. Pathol.* (1993) 46:750–753.

*Primary Examiner*—Michael G. Wityshyn
*Assistant Examiner*—Louise N. Leary
*Attorney, Agent, or Firm*—Karl Bozicevic; Carol L. Francis; Fish & Richardson

[57] ABSTRACT

A method for detecting *Helicobacter pylori* is disclosed which method involves contacting a sample suspected of containing *Helicobacter pylori* with a medium which provides for substantially selective growth of *Helicobacter pylori*, incubating the sample with the medium for a time sufficient for detection of *Helicobacter pylori* growth and detecting the growth and thereby reducing the presence of *Helicobacter pylori* within the sample. The methodology employs a wide range of a different culture mediums which are modified specifically for the selective growth and specific detection of *Helicobacter pylori*. A typical medium includes Columbia broth supplemented with urea and a pH indicator. The methodology provides for a relatively high degree of sensitivity (i.e., small numbers of bacteria present within a sample are detected) as well high selectivity (i.e., the method provides for a low percentage of false positives). Various kits used in connection with the method are designed so that they can be used by unskilled users in an "at home" setting. The kits and methodology are economical, easily used and provide highly accurate results within a relatively short period of time (e.g., 3 days or less).

14 Claims, No Drawings

DETECTION OF HELICOBACTER PYLORI

FIELD OF THE INVENTION

This invention relates generally to methods and compositions for the detection of bacteria within the samples and more particularly relates to methods, compositions and kits which provide for convenient, selective and sensitive methodology for detecting *Helicobacter pylori*.

BACKGROUND OF THE INVENTION

The invention relates to methods and compositions for the detection of *Helicobacter pylori*.

*Helicobacter pylori* is a urease-positive, microaerophilic, Gram-negative bacterium associated with gastritis, chronic gastritis, peptic ulcer disease, and gastric tumors in humans (Drumm et al. 1987 *N. Engl. J. Med.* 316:1557–1561; Jones et al. 1984 *J. Clin. Pathol.* 37:1002–1006; Marshall et al. 1984 *Lancet* i:1311–1315).

Attempts to detect *Helicobacer pylori* in clinical samples by culture of the organism have met with limited success due to the fastidious nature of the organism and the difficulties inherent in its selective growth. These problems are further complicated by the low number of organisms which may be present in the typical clinical sample, even when the sample is obtained by biopsy of gastric material. Attempts to diagnose *Helicobacter pylori* infection by detection of the organism in a sample obtained by less invasive techniques (e.g. saliva) has previously provided inconsistent results (Ferguson et al. 1993 *J. Clin. Microbiol.* 31:2802–2804). Serological diagnostic methods are more sensitive, but are not necessarily indicative of an active infection. Thus, there is a need for a simple, rapid detection method for detection of *Helicobacter pylori* which is not labor intensive and does not require growth conditions which can only be simulated in a laboratory setting.

SUMMARY OF THE INVENTION

A method for detecting *Helicobacter pylori* is disclosed which method involves contacting a sample suspected of containing *Helicobacter pylori* with a medium which provides for substantially selective growth of *Helicobacter pylori*, incubating the sample with the medium for a time sufficient for detection of *Helicobacter pylori* growth and detecting the growth and thereby reducing the presence of *Helicobacter pylori* within the sample. The methodology employs a wide range of a different culture mediums which are modified specifically for the selective growth and specific detection of *Helicobacter pylori*. A typical medium includes Columbia broth supplemented with urea and a pH indicator. The methodology provides for a relatively high degree of sensitivity (i.e., small numbers of bacteria present within a sample are detected) as well high selectivity (i.e., the method provides for a low percentage of false positives). Various kits used in connection with the method are designed so that they can be used by unskilled users in an "at home" setting. The kits and methodology are economical, easily used and provide highly accurate results within a relatively short period of time (e.g., 3 days or less).

In a preferred embodiment, a clinical sample suspected of containing *Helicobacter pylori* is placed in medium and subjected to conditions which provide substantially selective growth of *Helicobacter pylori*. The bacterium is detected by activity of the enzyme urease, which is produced by *Helicobacter pylori*. Urease catalyzes the conversion of urea to ammonium which, in turn, causes an increase in the pH of the growth medium. The pH change is detected by means of an indicator which provides a change in medium color over an appropriate pH range.

The present invention also provides growth media for the substantially selective growth of *Helicobacter pylori*. Use of these growth media avoids the need for growth of *Helicobacter pylori* under artificial $CO_2$ environments, such as in a $CO_2$-enriched tissue culture incubator or in a CampyPak® specifically designed to provide a microaerophilic environment for growth of Campylobacter species. The growth media described herein allow for substantially specific growth of *Helicobacter pylori* from a variety of samples, including clinical samples such as saliva, under a wide range of temperatures and under normal, ambient atmospheric conditions, e.g. 15° C. to 40° C., preferably about 23° C. to 37° C. and at normal atmospheric pressure plus or minus 20° in substantially normal air. (i.e., normal concentrations of oxygen, $CO_2$ and nitrogen.

The invention also features a kit for use in the detection of *Helicobacter pylori*, particularly in a clinical sample. The kit is appropriate for use in a laboratory, a physician's office or at home by an individual. The kit provides a sample-receiving receptacle (container) containing a medium substantially selective for growth of *Helicobacter pylori* and a means for closing the container, preferably so as to provide a substantially microaerophilic environment within the container. The kit may also comprise a means for collecting an appropriate volume of saliva or other clinical sample for testing in the kit.

An object of the invention is to provide a method for the detection of *Helicobacter pylori* which method involves incubating a sample of *Helicobacter pylori* on a medium which provides for substantially selective growth of *Helicobacter pylori* and thereafter detecting the presence of *Helicobacter pylori* growth on the medium.

Another object of the invention is to provide for medium compositions which provide for selective growth of *Helicobacter pylori* which compositions preferably include indicators such as pH indicators which allow for the direct detection of *Helicobacter pylori* growth on the medium.

Another object of the invention is to provide for kits for the detection of *Helicobacter pylori* which kits include a container for holding a sample and medium for growth of *Helicobacter pylori* on the surface of the medium and detection means for allowing for the detection of *Helicobacter pylori* growth on the medium.

An advantage of the present invention is that the methodology can be easily and economically carried out by substantially untrained individuals in an at home setting.

A feature of the present invention is that a conventional growth medium can be readily modified for use in connection with the invention.

These and other objects, advantages and features of the present invention will become apparent to those persons skilled in the art upon reading the present dislosure and reviewing the formulations and examples for and made a part hereof. Before the present assay methodology and compositions of the present invention are described, it is to be understood that this invention is not limited to the particular methodology and compositions disclosed as such methods and compositions made, of course, vary. It is also to be understood that the terminology used herein in with the purpose of describing particular embodiments only, and is not intended to limit the scope of the present invention which will be limited only by the appended claims.

It must be noted that as used herein and in the appended claims, the singular forms quote "A", "and", and "the" include plural referents unless the context clearly dictates otherwise. Thus, for example, referents to "a growth medium" includes mixtures of different growth mediums, "referens to antibacterial agent" includes one or more antibacterial agents, and "referents to the method of detection" or "the assay methodology" includes one or more methods of the type generally known to those skilled in the art and so forth. Although the invention is at times described in connection with specific medium and formulations it maybe used with a wide range of different formulations which provide for selective growth of *Helicobacter pylori*.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the prefered methods and materials are now described. All publications mentioned herein are incorporated herein by reference to describe and disclose specific information for which the reference was sited in connection with.

DEFINITIONS

By "catalase" is meant an enzyme, particularly an enzyme produced by *Helicobacter pylori*. Catalase catalyzes the conversion of hydrogen peroxide to water and oxygen. Catalase activity may generally be detected by the liberation of oxygen bubbles when placed in hydrogen peroxide.

By "*Helicobacter pylori*" is meant all strains of the bacterium *Helicobacter pylori*, as well as other members of the genus Helicobacter which produce urease and may be associated with a gastrointestinal disorder. *Helicobacter pylori* are microaerophilic, Gram-negative organisms which appear curved in tissue sample, and are more often rod-like, U-shaped or circular in culture. *Helicobacter pylori* have a tuft of polar, sheathed flagelli and exhibit optimal motility in a highly viscous milieu such as that found in the gastric mucous. *Helicobacter pylori* exhibit very high urease and catalase activity and do not metabolize sugars.

By "gastrointestinal disorder" is meant any disease or other disorder of the gastrointestinal tract of a human or other mammal. Such gastrointestinal disorders include, for example: disorders not manifested by presence of ulcerations in the gastric mucosa (non-ulcerative gastrointestinal disorder), including chronic or atrophic gastritis, gastroenteritis, non-ulcer dyspepsia, esophageal reflux disease, gastric motility disorders, and peptic ulcer disease (e.g. gastric and duodenal ulcers). In particular, "gastrointestinal disorder" refers to such disorders of the upper gastrointestinal tract caused or mediated by bacteria, particularly *Helicobacter pylori* or other members of the genus Helicobacter which produce the enzyme urease and are associated with gastrointestinal disorders.

By "gastritis" is meant inflammation of the stomach mucosa. The clinical symptoms associated with gastritis include a broad range of poorly-defined, and generally inadequately treated, symptoms such as indigestion, "heart burn" dyspepsia and excessive eructation. A general discussion of gastritis appears in Sleisenger and Fordtran (1989) In: *Gastrointestinal Disease*, 4th Ed., Saunders Publishing Co., Philadelphia, Pa., pages 772–902.

By "peptic ulcer" is meant ulceration and lesions of the mucous membrane of the esophagus, stomach, or duodenum which are characterized by loss of tissue due to the action of digestive acids and pepsin or other factors, such as *Helicobacter pylori* infection.

By "test sample" is meant any sample suspected of containing *Helicobacter pylori*, including clinical samples.

By "clinical sample" is meant a sample collected from a mammal, particularly a human, suspected of having an *Helicobacter pylori* infection. Clinical samples for detection of *Helicobacter pylori* may originate from a variety of sources including saliva, gastrointestinal secretions, gastric material (e.g., material collected by gastric biopsy), or stool. Preferably, the clinical sample is saliva.

By "gastric material" is meant any material obtained directly or indirectly from the upper gastrointestinal tract of a human or other animal. Such materials include, for example, gastric epithelium, gastric mucosa, and digestive fluids.

By "medium" is meant a liquid, semisolid, and/or solid composition suitable for growth of microorganisms. Medium as used herein generally refers to medium which is substantially selective for growth of *Helicobacter pylori*, including all formulations described herein and acceptable variations thereof. The medium preferrably consists essentially only of the components needed for the growth of *Helicobacter pylori* and is specifically lacking in components required for the growth other common microorganisms.

By "growth conditions" is meant the temperature and atmospheric condition (e.g. $CO_2$ concentration) at which a sample or culture is maintained. Growth conditions may also pertain to such variables as light, osmotic conditions in growth medium, and physical state of the sample or culture.

By "medium substantially selective for *Helicobacter pylori*" or "growth conditions substantially selective for *Helicobacter pylori*" is meant medium or growth conditions which provide a selective advantage for growth of *Helicobacter pylori* relative to other microorganisms which may be present. Medium and/or growth conditions substantially selective for *Helicobacter pylori* may support the growth of other microorganisms, providing that growth of these microorganisms does not interfere with growth of *Helicobacter pylori* or cause false positive or false negative results in the detection of *Helicobacter pylori*. Substantially selective media and/or growth conditions may be based upon, for example, nutrient requirements, antibiotic resistance, sensitivity to oxygen, $CO_2$ concentration, and temperature.

By "pH indicator" is meant any means by which a change of the acidity or basicity of a sample may be detected (e.g. pH meter, color indicator). Of particular interest are pH indicators which change color in response to an increase of pH and may be employed in either a liquid, semisolid, or solid bacterial growth medium.

By "effective concentration" is meant a concentration of a composition sufficient to achieve a desired effect. For example, an effective concentration of a pH indicator for use in the present invention is a concentration which effects a readily-discernible color change (preferably with the unaided eye) in the presence of ammonium in a medium substantially selective for growth of Helicobacter pylori.

By "antibiotic" is meant a composition which selectively inhibits growth of microorganisms. Antibiotics include both antibacterial and antifungal compositions.

By "urease" is meant an enzyme, particularly an enzyme produced by *Helicobacter pylori*, which catalyzes the conversion of urea into ammonium and carbon dioxide. Urease activity causes an increase in the pH of the medium or other environment in which the enzyme is located.

*Helicobacter pylori*

*Helicobacter pylori* produces urease, an enzyme which catalyzes the conversion of urea into ammonium and carbon dioxide. The production of ammonium results in an increase in the pH of the *Helicobacter pylori* growth medium. Therefore, the presence of *Helicobacter pylori* in a clinical sample may be detected by culturing the sample in a substantially selective growth medium and detecting an increase in the pH of the medium.

Culture media for substantially selective growth of *Helicobacter pylori*

The culture media which may be used in the subject method may vary substantially, but will normally contain a bacterial growth medium formulation, urea, and a pH indicator. Several conventional bacterial growth media may be modified for use in the subject method. Table I provides a detailed description of the exemplary media which have been successfully used in the detection assay. All values are based on a 1 liter volume of medium, unless indicated otherwise.

Although the specific formulations for growth medium listed below provide specific numbers in terms of the gram amount of each component present in a liter volume of medium it should be noted that the present invention is not specifically restricted to these amounts. In particular, variations in the range of plus or minus 10°, more preferably plus or minus 5° are acceptable and can be used in order to provide for selective growth of *Helicobacter pylori* when the formulation is used in connection with other components disclosed herein.

TABLE I

Bacterial Growth Media and Components For Use in the Detection Assay

Columbia Broth (pH 7,4)
0.1 g L-cysteine HCl
2.5 g glucose
1% IsoVitaleX
0.012 g $FeSO_4$
10.0 g pancreatic digest of casein
8.0 g peptic digest of animal tissue
0.05 g $MgSO_4$ Magnesium sulfate
0.1 g sodium citrate
5.0 g sodium chloride
2.86 g Tris(hydroxymethyl) aminomethane
0.83 g Tris(hydroxymethyl) aminomethyl HCl
5.0 g yeast extract
  Columbia Blood Agar Base
15 g agar
10.0 g brain heart infusion
10 g Bacto-pantone
1 g corn starch
5.0 g NaCl
3 g tryptic digest of beef heart
  Columbia Agar Base
13.5 g agar
3.0 g beef extract
1.0 g corn starch
12.0 g pancreatic digest of casein
5.0 g pepaic digest of animal tissue
3.0 g yeast extract
5.0 g NaCl
  Trypticase Soy Broth (pH 7.3)

10% v/v fetal calf serum
2.5 g glucose
1% v/v IsoVitaleX
17.0 g pancreatic digest of casein
3.0 g papaic digest of soybean meal
2.5 g $K_2HPO_4$
5.0 g NaCl
  Trypticase Soy Agar (pH 7.3)
15.0 g beef heart infusion
15.0 g pancreatic digest of casein
5.0 papaic digest of soybean meal
5.0 g NaCl
  Mueller-Hinton Broth (pH 7.3)
3.0 g beef extract
1.5 g starch
17.5 g acid hydrolysate of casein
10% v/v fetal calf serum
  Brain Heart Infusion Broth (pH 7.4)
6.0 g beef heart infusion
10% v/v fetal calf serum
3.0 g glucose
1% IsoVitaleX
14.5 g pancreatic digest of gelatin
6.0 g peptic digest of animal tissue
5.0 g NaCl
2.5 g $Na_2HPO_4$
  Brain Heart Infusion Agar
15 g agar
25.0 g beef heart infusion
20.0 g calf brain
2.0 g glucose
10 g protease peptone
5.0 g NaCl
2.5 g $Na_2HPO_4$
  Heart Infusion Agar (pH 7.4)
15 g agar
500 g beef heart infusion
10.0 g Bacto-Tryptose
5.0 g NaCl
  Brucella Broth (pH 7.0)
10% w/v fetal calf serum
1.0 g glucose
1% IsoVitaleX
10.0 g pancreatic digest of casein
10.0 g peptic digest of animal tissue
5.0 g NaCl
0.1 g sodium bisulfite (negative control)
2.0 g yeast extract
  Brucella Agar
15.0 g agar
1.0 g glucose
20.0 g peptic digest of animal tissue
5.0 g NaCl
0.1 g sodium bisulfite
2.0 g yeast extract As is evident from the bacterial growth medium formulations described in Table I, each medium comprises The preferred detection medium for the assay will be of the following general formula:

100 ml bacterial growth medium (selected from Table I)
10% v/v fetal calf serum (optional)
1% IsoVitaleX (optional)
5 mg/l trimethoprim (optional)
4 mg/l amphotericin (optional)
6 mg/l vancomycin (optional)
2% w/v urea
0.01 g or 0.0001 g phenol red Preferably, the medium will be of the general formulation comprising in one liter of medium:
a) 0.09 g to 0.11 g L-cysteine HCl,
b) 2.25 g to 2.75 g glucose,
c) 0.9% to 1.1% IsoVitaleX,
d) 0.011 g to 0.013 g $FeSO_4$,
e) 9.0 g to 11.0 g pancreatic digest of casein,
f) 7.8 g to 8.2 g peptic digest of animal tissue,
g) 0.045 g to 0.055 g MgSO4,
h) 0.09 g to 0.11 g sodium citrate,
i) 4.5 g to 5.5 sodium chloride,
j) 2.57 g to 3.15 g Tris(hydroxymethyl) aminomethane,
k) 0.3 to 0.36 g aminomethyl HCl,
l) 4.5 g to 5.5 g yeast extract,
m) 1.8% to 2.2% urea, and
n) 0.001 g to 0.01 g pH indicator; and More preferably, the medium employed in the detection assay will be Columbia Urease Test Broth (pH 6.8) having the formula:
100 ml Columbia broth (described in Table I)
10% v/v fetal calf serum (optional)
1% v/v IsoVitaleX (optional)
2% w/v urea
0.001 g w/v phenol red
1X PBS (to adjust volume to 1 liter)
0.4 mg/100 ml trimethoprim
0.6 mg/100 ml amphotericin
0.6 mg/100 ml vancomycin Columbia Urease Test Agar may be made by the addition of 1.5% agar and 0.1% yeast extract to the above formulation for Columbia Urease Test Broth. For all formulations described herein, the final volume of the medium is adjusted to 1 liter with either 1X phosphate-buffered saline (PBS) (pH 6.8) or with water and the pH adjusted to 6.8 with hydrochloric acid, if necessary. All media components are commercially available. IsoVitaleX® is an amino acid supplement containing (per liter) 100.0 g glucose, 25.9 g L-cysteine-HCl, 10.0 g L-glutamine, 1.0 g adenine, 0.1 g thiamine pyrophosphate, 0.1 g vitamin $B_{12}$, 0.03 g guanine-HCl, 0.02 g $Fe(NO_3)_3(H_2O)$, 0.013 g p-aminobenzoic acid, 0.003 g thiamine-HCl.

The pH indicators used in this invention are weak acids, with sharply different colors in their dissociated (ionized) and undissociated (neutral) states. The indicators useful in the practice of the invention have $pK_a$ values of from about 6.5 to about 8.5, preferably from about 7.0 to about 8.0. The color exhibited by the indicator in the medium will depend upon the pH of the composition, the particular indicator used, and the dissociation constant ($K_a$) for that indicator (e.g. $pK_a = log_{10}K_a$). As the color exhibited by the indicator changes over a range of pH values ($pH = log_{10}[H^+]$), the indicators useful in the medium change color over a pH range of from about 5.5 to about 9.0, preferably from about 6.5 to about 8.5.

Indicators which may be used in the composition of the invention include p-nitrophenol, bromothymol blue (dibromothymolsulfonphthalein), phenol red (phenolsulfonphthalein), neutral red (2-methyl-2-amino-6-dimethylaminophenazine), quinoline blue (cyanine), cresol red (o-cresolsulfonphthalein), metacresol purple (m-cresolsulfonphthalein), and thymol blue (thymolsulfonphthalein). The concentration of indicator employed in the medium may vary, although the indicator will typically be present at a concentration of from about 1 to about 100 mgs per liter, usually about 0.5 to 60 mgs per liter, normally about 1 mg per liter. Phenol red is the preferred indicator for use in the present invention and will normally be present at a concentration of about 10 mg per liter.

The pH of the medium may be adjusted to a pH at least about one pH unit lower than the $pK_a$ of the indicator used (i.e., having a hydrogen ion concentration $[H^+]$ ten times less than (10% of) the hydrogen ion concentration in a solution having a pH equal to the $pK_a$ of the indicator). Preferably, the pH is adjusted to a pH about two pH units below the pKa of the indicator. Adjustment of the pH of the medium can be effected by addition of a base (e.g., sodium hydroxide) or an acid (e.g., hydrochloric or citric acid). Thus, preferably, the pH of the medium is adjusted to a pH of from about 5.0 to about 6.5, more preferably from about 5.0 to about 6.0. The pH of the final composition may be adjusted by the addition of a suitable buffer. Appropriate buffers (e.g. weak acid salts such as sodium bisulfate, sodium acetate, and sodium phosphate) are well known in the chemical art.

Alternative means for detecting the presence of Helicobacter pylori may be employed in place of a pH color indicator. For example, the presence of Helicobacter pylori may be detected by the action of the Helicobacter pylori enzyme catalase. Catalase activity may be generally detected by the production of oxygen bubble when the bacterium is placed in hydrogen peroxide. Further alternative methods for detection of the presence of Helicobacter pylori include the relase of a radioactive label from a radoactively labeled substrate of urease (e.g. urea). Methods for the production of such radioactively labeled substrates are well known in the art. Growth of Helicobacter pylori may also be detected by colony formation on the substantially selective media described herein, particularly where the medium is substantially devoid of sugar.

The total amount of buffer incorporated in the medium will depend upon the total amount of urea present in the medium. Of particular important is that the buffer does not prevent sufficient change in medium pH resulting from hydrolysis of the urea by the urease of Helicobacter pylori. The buffer is preferably present at a concentration sufficient to prevent substantial changes in medium pH and accompanying spurious indicator color changes due to the action of components in the medium other than urease. Typically the buffer is present in the medium at concentrations of from about 50 to about 2000 mg per liter. Examples of buffers which may be used include Tris (hydroxymethyl)aminomethane and phosphate buffers. Buffer concentration includes the concentration of buffer salt(s) and acid(s) used to adjust medium pH. In some formulation the buffer may be omitted and the pH adjusted (e.g. by addition of hydrochloric acid).

The substantially selective medium for growth of Helicobacter pylori may comprise an antibiotic(s), such as antibacterial or antifungal compositions, which are capable of inhibiting growth of non-Helicobacter pylori microorganisms. Exemplary antibiotic compositions useful in this invention include trimethoprim (at about 2 to 15 mg per liter), amphotericin B (at about 2 to 10 mg per liter), and vancomycin (at about 2 to 6 mg per liter). Of particular importance is that the antibiotic(s) is not present in the medium at a concentration which may substantially inhibit Helicobacter pylori growth. Antibiotics may be used in the selective medium to prevent inhibition of Helicobacter pylori growth due to competition for nutrients with faster growing microorganisms present in the sample and to reduce the background which may result from growth of non-Helicobacter, urease-producing organisms such as Proteus mirabilis and Klebsiella pseudomonas. Use of antibiotics may thus reduce the incidence of false negative or false positive results.

The medium may be in liquid, semisolid, and/or solid form, preferably the medium will be either liquid or biphasic (both liquid and solid). Where a semisolid or solid form is desired, the medium may comprise a gelling agent, so that the medium is in a semisolid or solid state at ambient conditions. A particularly preferred gelling agent is agar, present at a level of from about 5 to about 50 g per liter, usually from about 10 to about 20 g per liter, typically 15 g per liter. Agar is commercially available from a variety of sources and the methods for its use are well known in the art.

Patient identification

Individuals who should be tested for *Helicobacter pylori* infection include those with symptoms of gastritis or other gastrointestinal disorders which may be associated with *Helicobacter pylori* infection. Symptoms associated with gastritis are generally non-specific and include epigastric pain and "heart burn". Alternatively, it may be desirable to test an asymptomatic individual, particularly where the individual may have been exposed to *Helicobacter pylori* or has a condition rendering the individual susceptible to infection.

Test samples

Any sample suspected of containing *Helicobacter pylori* may be tested by the method of the present invention. Generally, test samples will be clinical samples derived from a mammal, particularly a human. Appropriate samples for *Helicobacter pylori* testing include saliva, gastric material (e.g. obtained by gastric biopsy), gastrointestinal secretions, and stool. The preferred clinical sample is saliva, more preferably oral-pharynx-derived saliva, as this sample is easily obtained without invasive techniques. The samples described above may be obtained by appropriate methods well known in the art, such as endoscopy or biopsy, as required for collection of gastric material derived from the stomach lining.

The volume of the sample required for detection of *Helicobacter pylori* will depend upon the number of *Helicobacter pylori* bacteria which may be present in the particular sample. For example, *Helicobacter pylori* may be readily detectable in smaller amounts of samples derived from gastrointestinal secretions than in samples derived from saliva or stool. As the growth media used in the present invention allow for substantially selective growth of *Helicobacter pylori*, the sample may need only contain a single *Helicobacter pylori* bacterium in order to provide an accurate, positive result. Generally, the sample volume must be large enough to allow for sufficient contact of the sample with the medium. Where the sample is collected from saliva, the volume of sample for testing may range in volume from a few microliters (1 to 2 μl) to about 500 μl. Saliva samples of 1 μl to 10 μl have proved sufficient for accurate detection of *Helicobacter pylori* in 8 out of 10 infected individuals (see Example).

Prior to testing the samples may be treated to enhance *Helicobacter pylori* detection. For example, if the sample constitutes digestive fluids, then a preferred optional step is testing the pH of the sample. Preferably, the sample is contacted with a pH-test composition, preferably an aqueous solution of the particular indicator used in the substantially selective medium (without urea) which is adjusted to the same pH as the selective medium. If the sample is of a neutral to acidic pH, then the sample may be used directly in the detection method. If the sample is of a basic pH, then it may be desirable to adjust the pH of the sample by the addition of acid. In addition, where a sample from a gstric biopsy is employed, it may be desirable to mince or homogenize the material prior to testing.

Detection of *Helicobacter pylori*

After the sample is collected, the sample is contacted with a medium substantially selective for *Helicobacter pylori* growth and which also comprises a pH indicator. The amount of medium used in the assay may vary considerably. Preferably, the ratio of sample volume to medium will not exceed about 1:2, particularly where the medium is liquid. Where the medium used is semisolid or solid, the sample can either be spread upon the medium surface or inserted directly into approximately the center of the medium. Where the medium used is liquid, the sample may be agitated to mix the sample and medium components. Inoculation of the medium with sample will preferably be performed under sterile conditions so that the sample is not contaminated with microorganisms in the environment (e.g. bacteria from human skin).

It may be desirable to perform the detection assay with both a test and a control sample. Examples of appropriate control samples may include a clinical sample obtained from an uninfected individual, a sample having no urease-positive bacteria or a sample known to contain a urease positive bacterium. Alternatively, the control sample may be a sample having an alterations to the substantially selective medium describe above. For example, a preferred negative control comprises contacting a second aliquot of the test sample with a substantially selective medium which further comprises an inhibitor of *Helicobacter pylori*, e.g., sodium bisulfite or sodium sulfite. Preferably the medium for the negative control sample will comprise about 0.2 mM sodium bisulfite and/or 0.2 mM sodium sulfite. The negative control sample is then treated in the same manner as the test sample.

After the medium is inoculated with sample, the container holding the medium is then covered (e.g. with a screw cap or cap) to provide a substantially microaerophilic environment within the container. The inoculated medium is then incubated for a time ranging from a few hours to several days, or until a change in medium color (corresponding to the color change of the pH indicator) is detected. Incubation may be carried out at a variety of temperatures, which may affect the time required for detection of a color change (pH change). For example, if the inoculated medium is incubated at 37° C., the pH change may be detected within about 4 to 6 hours, usually no more than 24 hours; if incubated at 33° C., the pH change may be detected within about 12 to 24 hours, usually no more than 36 hours; and if incubated at 23°–25° C. (room temperature), the pH change may be detected within 2 to 3 days.

Where a control sample is used in addition to the test sample, any color change detected in the test sample is compared to any color change of the control sample. Where a negative control comprises a second aliquot of the test sample inoculated in a substantially selective medium comprising an *Helicobacter pylori* inhibitor, if the negative control sample changes color after the same period of incubation as the test sample, then the color change detected in the test sample is not caused by *Helicobacter pylori*, but by some other urease-positive bacterium preset in the test sample. Where the selective medium comprises antibiotics, the likelihood that the negative control sample would change color after incubation is unlikely, as this would require that the test sample contain a urease-positive bacterium which is resistant to any or all antibiotics present in the medium. Where the medium used contains multiple antibiotics, and thus the likelihood that a urease-positive, multiply drug resistant bacterium other than *Helicobacter pylori* would be present in the sample, the negative control may be omitted without significantly affecting the accuracy of the assay results.

Where phenol red is used as the pH indicator and *H. pylori* is in the sample, the color change detected is a shift from yellow (or the color of the medium when sterile) to pink or red. If the medium is solid or semisolid, and the sample was not thoroughly mixed into the medium, the color change may be readily detected by comparing the color of the medium in direct contact with the sample with the color of the medium at a site distant from the site of sample contact. If there is only a slight color change in the inoculated medium, or there is some uncertainty as to whether the color of the inoculated medium differs significantly from the color of sterile medium, the inoculated medium should be incubated further until a color change is apparent. If there is no change in the color of the inoculated medium after incubation for 36 hours to 3 days (depending upon incubation temperature), the sample is negative for *Helicobacter pylori*.

The assay of the subject invention provides for both a very high sensitivity and a high specificity of detection of *Helicobacter pylori*. The subject method provides for a sensitivity such that at least 80%, preferably at least 98% of the samples determined to be positive are true positive, (e.g., the samples actually contain *Helicobacter pylori* and the individual from whom the samples were collected have a *Helicobacter pylori* infection). The subject method also provides that where the sample contains microorganisms other than *Helicobacter pylori*, at least 80%, preferably at least 98% of the samples determined to be negative are true negative samples (e.g., do not contain *Helicobacter pylori* and the individual from whom the sample was collected is not infected with *Helicobacter pylori*).

After testing, the *Helicobacter pylori* which may be present in the sample may be recovered and cultured for further study (e.g. determination of antibiotic resistance/susceptibility). If desired, the organisms may be recovered from the assay medium and the presence of *Helicobacter pylori* secondarily confirmed by testing other characteristics of *Helicobacter pylori* (e.g., catalase activity). From the results of the subject method, as well as subsequent tests performed on the recovered organisms, a diagnosis may be determined and an appropriate therapy prescribed. The effectiveness of the treatment may be followed by again testing samples from the patient with the subject method. Thus, the present invention provides a convenient means for following a patient recovering from *Helicobacter pylori* infection and/or treatment efficacy. The subject method thus may be readily applied for mass screening of symptomatic or asymptomatic individuals. The method of the invention may be easily automated and the results of the assays may be read by a variety of detection methods (e.g., spectrophotometry). This feature of the detection method makes it possible for medium inoculated with a test sample to be forwarded to a facility where the assay results can be determined quickly by automation. Furthermore, practice of the subject method requires neither special equipment nor professional training and thus may be used as a self-diagnostic test.

Kits

Kits for use in the practice of the method of the subject invention may comprise a sample-receiving receptacle (container) which contains a sufficient amount of a substantially selective growth medium (described above) which comprises a pH indicator. The amount of medium contained in the container will be sufficient for testing of at least one sample, preferably a saliva sample the medium in the container may be provided in a variety of forms such as liquid, biphasic (liquid and solid), and semisolid. Biphasic forms of the medium in the container may be provided as liquid medium layered upon solid medium or a layer of solid medium sandwiched between two layers of liquid medium. The container may further comprise a cover (e.g. cap, screw cap, lid, film) to provide a substantially microaerophilic environment inside the container. The kit may further comprise a device for collection of the sample (e.g. a sterile pipette or dipstick for saliva collection). For example, the container may have a cap which comprises a sterile plastic dipstick affixed to the interior of the cap. The cap may be removed by the user and the plastic dipstick contacted with the subject's saliva to collect a sample. The plastic dipstick with the sample is then placed within the container and, simultaneously, the cap affixed in place on the container. When the cap is in the closed position, the plastic dipstick is forced into contact with the medium and the medium is inoculated with the sample.

The container containing the inoculated medium is then incubated for an appropriate amount of time. The change in medium color is observed and correlated with the presence of *Helicobacter pylori* in the sample. The kit may further comprise a color strip for comparison of the color of positive and negative controls with the test sample. The kit for detection of *Helicobacter pylori* may be used in a laboratory, a physician's office, or may be used in a private residence for self-diagnosis of *Helicobacter pylori* infection.

EXAMPLES

The following example is provided so as to give those of ordinary skill in the art a complete disclosure and description of how to perform the method of the subject invention and how to make and use the media of the invention and are not intended to limit the scope of what the inventors regard a their invention. Efforts have been made to insure accuracy with respect to the specific given such as the concentration of media components, but some experimental errors and deviations should be accounted for.

Detection of *Helicobacter pylori* in Human Saliva

Saliva samples were collected from 21 individuals (18 male, 13 female) for testing for the presence of *Helicobacter pylori* in a controlled, double-blind study. In order to collect saliva samples, subjects were asked to spit into a test tube containing a solid (agar-containing) formulation of the Columbia Urease Test Broth (described in Table I). The approximate volume of the saliva samples was from about 500 µl to about 5 ml. In addition to the saliva sample, a serum sample was also collected from each individual to test for the presence of anti-*Helicobacter pylori* antibodies. Gastric biopsy material, which was additionally collected from several of the individuals in the study, was examined for gastritis pathology associated with *Helicobacter pylori* (King et al. 1992 *Gastroenterology* 102:A97), and the presence of *Helicobacter pylori* infection confirmed by PCR (Liu et al. 1991 *American College of Gastroenterology* 86:1314; Liu et al. 1992 *Gastointestinal Endoscopy* 38:237), culture, and serology using Quidel's QuickVue (ELISA) test (Dooley et al. 1989 *New Engl. J. Med.* 321:1562).

The medium inoculated with the saliva samples was then capped and were subsequently incubated at 37 degrees C. for 8 to 12 hours (without an enriched $CO_2$-environment). After incubation, the samples were then examined for a shift in color from yellow to pink or red. Samples which did not show any color change were replaced in the incubator for a total incubation time of about 72 hours. If a color change was not observed by this time, the sample was designated negative. The results of this study, and comparison of the results of the detection method of the invention to conventional detection methods is provided in Table II.

TABLE II

Comparison of Methods for Detection of *Helicobacter pylori*

| Patient | Gender | Serology | Gastric Mucosa Biopsy | Pathology | Culture | PCR | Saliva Culture |
|---|---|---|---|---|---|---|---|
| A | f | + | + | + | + | + | + |
| B | f | + | + | + | + | + | + |
| B' (after treatment) | | + | | − | | | − |
| C | m | + | ND | | | | + |
| D | m | + | ND | | | | + |
| E | m | + | ND | | | | + |
| F | f | + | + | + | + | + | + |
| G | f | + | + | ND | ND | ND | + |
| G' (after treatment) | | + | | | | | + |
| H | f | + | + | + | + | + | ND |
| H' (after treatment) | | + | + | − | − | − | − |
| I | f | + | ND | | | | + |
| J | m | + | ND | | | | + |
| K | f | + | ND | | | | − |
| L | m | + | ND | | | | + |
| M | f | + | ND | | | | + |
| N | f | + | ND | | | | + |
| O | f | + | ND | | | | + |
| P | m | − | + | − | − | − | − |
| Q | m | − | ND | | | | − |
| R | f | − | ND | | | | − |
| S | m | − | ND | | | | − |
| T | f | − | ND | | | | − |
| U | f | − | ND | | | | − |

ND = Not Done

Of the 21 individuals tested, 15 were infected with *Helicobacter pylori* as determined by serology. When samples of saliva were examined by the subject method, 14 of the 15 infected individuals produced positive saliva cultures. When a second saliva culture was obtained from the individual K, who initially tested positive by serology and negative by the subject method, the sample was positive. Patients B, G and H were followed after treatment. Both patients B and H tested negative after treatment for *Helicobacter pylori* infection. Even after multiple courses of treatment, patient G tested positive by both serology and the subject method.

While the present invention has been described with reference to specific substantially selective medium for growth of *Helicobacter pylori*, kits, and methods of detection of *Helicobacter pylori* in a sample, it should be understood by those skilled in the art that various changes may be made and equivalence may be substituted without departing from the true spirit and scope of the invention. In addition, many modification may be made to adapt a particular situation, test sample, method or method step or steps to the objective, spirit and scope of the invention. All such modifications are intended to be within the scope of the claims appended hereto.

What is claimed is:

1. A method for detection of a *Helicobacter pylori* strain comprising the steps of:
   contacting a saliva sample suspected of containing *H. pylori* directly with a medium selective for growth of *H. pylori*, said medium having a pH of about 5.5 to 7.5; and
   incubating the sample for a time sufficient for detection of *H. pylori* growth wherein the method provides for detection of *H. pylori* growth in at least 80% of true positive samples.

2. The method according to claim 1, wherein the method provides a sensitivity for detecting *H. pylori* at a concentration of 1 bacterium per 1 µl of saliva sample.

3. The method according to claim 1, wherein the method provides for detection of *H. Pylori* in 98% of true positive samples.

4. The method according to claim 1, further comprising a pH indicator for detecting pH and producing a color indicator.

5. The method according to claim 1, wherein detection of growth of *H. pylori* is by detection of the release of a radioactive label upon cleavage of labeled urease substrate.

6. The method according to claim 1 wherein the medium is substantially devoid of sugar.

7. A method for detection of a *Helicobacter pylori* strain, said method comprising the steps of:
   contacting a saliva sample suspected of containing *H. pylori* directly with a medium selective for growth of *H. pylori*, said medium comprising in one liter of medium:
   a) 0.09 g to 0.11 g L-cysteine HCl,
   b) 2.25 g to 2.75 g glucose,
   c) 0.9% v/v to 1.1% v/v IsoVitaleX,
   d) 0.011 g to 0.013 g $FeSO_4$,
   e) 9.0 g to 11.0 g pancreatic digest of casein,
   f) 7.8 g to 8.2 g peptic digest of animal tissue,
   g) 0.045 g to 0.055 g MgSO4,
   h) 0.09 g to 0.11 g sodium citrate, i) 4.5 g to 5.5 g sodium chloride, j) 2.57 g to 3.15 g Tris(hydroxymethyl) aminomethane, k) 0.3 to 0.36 g aminomethyl HCl, l) 4.5 g to 5.5 g yeast extract, m) 1.8% w/v to 2.2% v/v urea, and n) 0.001 g to 0.01 g pH indicator, said medium having a pH of about 5.5 to 7.5; and incubating the sample for a time sufficient for detection of a change in medium color caused by the enzymatic activity of urease produced by *H. pylori;* wherein a change in medium color indicates the presence of *H. pylori* in the sample.

8. The method according to claim 7, wherein said incubating is at 23–25 degrees C. and said change in medium color is detected in 2 to 3 days.

9. The method according to claim 7, wherein said incubating is at 33 degrees C. and said change in medium color is detected in 4 to 6 hours.

10. The method according to claim 7, wherein said incubating is at 37 degrees C. and said change in medium color is detected in 4 to 6 hours.

11. A composition for use in detection and substantially selective growth of *Helicobacter pylori* in a sample, said composition comprising in one liter of medium:

a) 0.09 g to 0.11 g L-cysteine HCl, b) 0.9% v/v to 1.1% v/v IsoVitaleX, c) 0.011 g to 0.013 g FeSO$_4$, d) 9.0 g to 11.0 g pancreatic digest of casein, e) 7.8 g to 8.2 g peptic digest of animal tissue, f) 0.045 g to 0.055 g MgSO$_4$, g) 0.09 g to 0.11 g sodium citrate, h) 4.5 g to 5.5 g sodium chloride, i) 2.57 g to 3.15 g Tris(hydroxymethyl) aminomethane, j) 0.3 to 0.36 g aminomethyl HCl, k) 4.5 g to 5.5 g yeast extract, l) 1.8% w/v to 2.2% w/v urea, and m) 0.001 g to 0.01 g pH indicator, with the proviso that the composition is substantially devoid of sugar.

12. A composition for detection and substantially selective growth of *Helicobacter pylori* in a sample, said composition comprising urea, a pH indicator, and a bacterial growth medium selected from the group consisting essentially of Columbia broth, Columbia blood agar base, Columbia agar base, trypticase soy broth, trypticase soy agar, Mueller-Hinton broth, brain heart infusion broth, brain heart infusion agar, heart infusion agar, Brucella broth, and Brucella agar, with the proviso that the composition is substantially devoid of sugar.

13. A kit for detection of *Helicobacter pylori* comprising:

a sample collection device.;

a sample receiving receptacle containing a medium for substantially selective growth of *H. pylori,* said medium comprising urea, a pH indicator, and a bacterial growth medium selected from the group consisting essentially of Columbia broth, Columbia blood agar base, Columbia agar base, trypticase soy broth, trypticase soy agar, Mueller-Hinton broth, brain heart infusion broth, brain heart infusion agar, heart infusion agar, Brucella broth, and Brucella agar, with the proviso that the medium is substantially devoid of sugar; and a cover for said receptacle.

14. A kit for detection of *Helicobacter pylori* comprising:

a sample collection device;

a sample receiving receptacle containing a medium for selective growth of *H. pylori,* said medium comprising in one liter of medium:

a) 0.09 g to 0.11 g L-cysteine HCl, b) 0.9% v/v to 1.1% v/v IsoVitaleX, c) 0.011 g to 0.013 g FeSO$_4$, d) 9.0 g to 11.0 g pancreatic digest of casein, e) 7.8 g to 8.2 g peptic digest of animal tissue, f) 0.045 g to 0.055 g MgSO4, g) 0.09 g to 0.11 g sodium citrate, h) 4.5 g to 5.5 g sodium chloride, i) 2.57 g to 3.15 g Tris(hydroxymethyl) aminomethane, j) 0.3 to 0.36 g aminomethyl HCl, d) 4.5 g to 5.5 g yeast extract, l) 1.8% w/v to 2.2% w/v urea, and m) 0.001 g to 0.01 g pH indicator, with the proviso that the composition is substantially devoid of sugar; and a cover for said receptacle.

\* \* \* \* \*